United States Patent
Nishiwaki et al.

(10) Patent No.: US 8,852,413 B2
(45) Date of Patent: Oct. 7, 2014

(54) BIOSENSOR

(75) Inventors: Naohide Nishiwaki, Seki (JP); Shoichi Miyamoto, Seki (JP); Akitsugu Inagawa, Seki (JP); Hironobu Murase, Seki (JP)

(73) Assignees: CCI Corporation, Gifu (JP); Ultizyme International Ltd., Tokyo (JP)

( * ) Notice: Subject to any disclaimer, the term of this patent is extended or adjusted under 35 U.S.C. 154(b) by 79 days.

(21) Appl. No.: 13/637,833

(22) PCT Filed: Mar. 30, 2011

(86) PCT No.: PCT/JP2011/058030
§ 371 (c)(1),
(2), (4) Date: Sep. 27, 2012

(87) PCT Pub. No.: WO2011/125750
PCT Pub. Date: Oct. 13, 2011

(65) Prior Publication Data
US 2013/0020196 A1    Jan. 24, 2013

(30) Foreign Application Priority Data
Mar. 31, 2010  (JP) .................................. 2010-081435

(51) Int. Cl.
*G01N 27/327* (2006.01)
*C12Q 1/00* (2006.01)

(52) U.S. Cl.
CPC ............ *G01N 27/3272* (2013.01); *C12Q 1/005* (2013.01)
USPC .................. 204/403.14; 435/287.1; 422/68.1; 422/82.01

(58) Field of Classification Search
USPC ...................... 204/403.01–403.15; 435/287.1; 422/68.1, 82.01
See application file for complete search history.

(56) References Cited

U.S. PATENT DOCUMENTS

| 6,117,289 A * | 9/2000 | Yamamoto et al. ...... 204/403.08 |
| 2003/0175841 A1 | 9/2003 | Watanabe et al. |
| 2009/0236222 A1 * | 9/2009 | Murase et al. ........... 204/403.14 |

FOREIGN PATENT DOCUMENTS

| JP | A-9-043190 | 2/1997 |
| JP | 2007259814 | * 10/2007 |
| JP | A-2009-244013 | 10/2009 |
| JP | A-2009-244014 | 10/2009 |
| WO | WO02/093151 | 11/2002 |
| WO | WO2006/104077 | 10/2006 |
| WO | WO2007/094354 | 8/2007 |

OTHER PUBLICATIONS

Machine translation JP2007259814, performed Jan. 9, 2014.*
Aki Tachibana, et al., "Characteristics of Multi-enzyme Electrode", CSJ: The Chemical Society of Japan Dai 73 Shuki Nenkai Koen Yokoshu, Sep. 10, 1997, p. 129.

* cited by examiner

*Primary Examiner* — Jennifer Dieterle
(74) *Attorney, Agent, or Firm* — Cesari and McKenna, LLP (57) ABSTRACT

A biosensor, comprising an insulating base plate, an electrode system containing at least a working electrode and a counter electrode and formed on the insulating base plate, and a sample-supplying section formed on the electrode system, wherein the sample-supplying section has a reaction layer comprising: a first reaction layer formed on the electrode system and containing at least a redox enzyme into which pyrroloquinoline quinone (PQQ), flavin adenine dinucleotide (FAD), or flavin mononucleotide (FMN) is incorporated as a prosthetic group; and a second reaction layer formed by applying, onto the first reaction layer, a solution including a lipid decomposing enzyme.

20 Claims, 5 Drawing Sheets

BIOSENSOR

CROSS REFERENCE TO RELATED APPLICATIONS

This application is a National Stage of International Application No. PCT/JP2011/058030 filed on Mar. 30, 2011, which claims priority to Japanese Application No. 2010-081435 filed Mar. 31, 2010. The contents of the prior applications are incorporated herein by reference in their entirety.

TECHNICAL FIELD

The present invention relates to biosensor, in particular, biosensor for measuring concentration of neutral fat. The invention relates specifically to a biosensor capable of determining the concentration of a specific component in a specific sample, such as living body sample, quantitatively and rapidly by use of enzyme reaction, in particular, such a biosensor for measuring the concentration of neutral fat.

BACKGROUND ART

In recent years, biosensors have been used in the field of medicine and others. Targets to be measured by biosensors are various chemical substances, examples of which include low molecular weight and high molecular weight molecules. In accordance with the target to be measured, the development of a biosensor having various functions has been advanced.

Hitherto, biosensors have been known which can easily attain quantitative determination without diluting or stirring a specific component (substrate) contained in living body sample, or food. Suggested is, for example, a biosensor obtained by: forming an electrode system having at least a working electrode and a counter electrode on an insulating base plate; laying, onto this electrode system, an enzyme reaction layer containing a redox enzyme and an electron receptor each immobilized with an immobilizing agent such as a hydrophilic polymer; next laying a filtrating layer (blood corpuscle removing layer) onto this enzyme reaction layer; and further covering this filtrating layer, from the above, with a cover to integrate these members into a unit.

By such biosensor, the concentration of substrate in a sample is quantitatively determined in the following manner: First, a sample solution, such as blood, is dropped onto the filtrating layer, and the resultant filtrate penetrates into the enzyme reaction layer. In this way, the redox enzyme and the electron receptor are dissolved in the sample solution so that an enzyme reaction advances between the substrate and the enzyme. By this enzyme reaction, the substrate is oxidized and simultaneously the electron receptor is reduced. After the enzyme reaction ends, the reduced electron receptor is electrochemically oxidized. From the oxidation current value obtained at this time, the concentration of the substrate in the sample solution can be calculated.

As a method for measuring neutral fat with biosensor, known is, for example, a method of determining neutral fat in sample quantitatively as follows: the neutral fat contained in sample solution is first decomposed into, for example, free fatty acid and glycerol with lipoprotein lipase (LPL). As shown in formulae (1) and (2) described below, glycerol generated therein can be quantitatively determined, using glycerol kinase (GK), and glycerol-3-phosphoric acid oxidase (GPO), or glycerol-3-phosphoric acid dehydrogenase (GPDH). In other words, the glycerol can be quantitatively determined by measuring decrease in the oxidized-form electron receptor, increase in the reduced-form electron receptor, or the quantity of dihydroxyacetone phosphoric acid, as shown in the following formulae. In particular, by measuring the quantity of the increase in the reduced-form electron receptor electrochemically, the glycerol can be quantitatively determined.

[Chemical formula 1]

(1)

(2)

However, each of three enzymes, i.e., lipoprotein lipase (LPL), glycerol kinase (GK), and glycerol-3-phosphoric acid oxidase (GPO), which are used in the above-mentioned neutral-fat-measurement is expensive.

In order to solve this problem, a biosensor, in which, as enzymes used in a decomposition reaction of neutral fat, two of neutral fat decomposing enzyme and glycerol dehydrogenase (GLDH) are used to decrease enzyme costs, is disclosed (Patent Literature 1). However, the biosensor of Patent Literature 1 is not sufficient about the measurement time, and in precision. Thus, it is desired to make the precision higher, and make the measurement more rapidly.

In the meantime, as a method using a single enzyme without effect of dissolved oxygen, known is a method as shown in a formula (3) described below, wherein NAD+ dependent glycerol dehydrogenase (NAD-GLDH) is used.

[Chemical Formula 2]

(3)

However, this reaction requires the addition of NAD+, which is expensive.

As a method for determining glycerol quantitatively, easily and inexpensively, known is a method using polyol dehydrogenase into which pyrroloquninoline quinone is incorporated as a prosthetic group (PQQ-PDH).

This method is performed in accordance with a reaction of a formula (4) described below; thus, the method has, for example, advantages that the determination is not affected by any dissolved oxygen, the reaction is simple, the use of plural enzymes is unnecessary, and the addition of expensive NAD+ is not required.

[Chemical Formula 3]

(4)

Considering the above matters, in order to supply a biosensor capable of measuring neutral fat with high precision in short time, reports have been hitherto made about biosensors in each of which a neutral fat decomposing enzyme and glycerol dehydrogenase are located in different layers, respectively (Patent Literatures 2 and 3). The biosensor of Patent Literature 2 has a structure having, on an electrode, a polymer layer containing GLDH and a hydrophilic polymer, and a filter layer containing a neutral fat decomposing enzyme carried on a filter paper, these two reaction layers being laminated in turn. The biosensor of Patent Literature 3 is characterized by having a structure having, on an electrode, a polymer layer containing GLDH and a hydrophilic polymer, and a nonwoven cloth layer containing a neutral fat decomposing enzyme carried on a nonwoven cloth, these two reaction layers being laminated in turn.

PRIOR ART

Patent Literatures

Patent Literature 1: WO 2006/104077 Pamphlet
Patent Literature 2: Japanese Patent Application Laid Open (JP-A) No. 2009-244013
Patent Literature 3: JP-A-2009-244014

SUMMARY OF INVENTION

Technical Problem

However, even according to the biosensors described in Patent Literatures 2 and 3, the measuring time is two minutes in Example (paragraph [0100] of Patent Literature 2, and paragraph [0100] of Patent Literature 3). In conclusion, the measuring time is not yet sufficiently short. Thus, a biosensor capable of making a measurement in a shorter time is desired.

Thus, the invention has been made to solve the problems, and an object thereof is to provide a biosensor capable of measuring the concentration of a specific component, such as neutral fat, in sample in a short period.

Solution to Problem

The inventors have eagerly made researches to solve the problems. As a result, the inventors have found that when a reaction layer is made into a bilayered structure, without using a carrier such as a filter paper or a nonwoven cloth, by the formation of a lipid-decomposing-enzyme-containing layer on a redox-enzyme-containing layer by applying a lipid-decomposing-enzyme-containing solution directly onto the redox-enzyme-containing layer, the rates of reactions by the two enzymes can be improved. Based on this finding, the invention has been achieved.

Accordingly, the above-mentioned object is attained by a biosensor comprising an insulating base plate, an electrode system containing at least a working electrode and a counter electrode and formed on the insulating base plate, and a sample-supplying section formed on the electrode system, wherein the sample-supplying section has a reaction layer comprising: a first reaction layer formed on the electrode system and containing at least a redox enzyme into which pyrroloquinoline quinone (PQQ), flavin adenine dinucleotide (FAD), or flavin mononucleotide (FMN) is incorporated as a prosthetic group; and a second reaction layer formed by applying, onto the first reaction layer, a solution including a lipid decomposing enzyme.

Advantageous Effects of Invention

The use of the biosensor of the invention makes it possible to measure the concentration of target component in a short period.

BRIEF DESCRIPTION OF DRAWINGS

FIG. 1 is an exploded perspective view of an embodiment of the biosensor of the invention.
FIG. 2 is a sectional view of the biosensor in FIG. 1.
FIG. 3 is an exploded perspective view of another embodiment of the biosensor of the invention.
FIG. 4 is a sectional view of the biosensor in FIG. 3.
FIG. 5 is a graph showing measured results of the neutral fat concentration in whole blood in each of Examples 1 and 2, and Comparative Example.
FIG. 6 is a graph showing measured results of the neutral fat concentration in whole blood in each of Examples 3 and 4.
FIG. 7 is a graph showing measured results of the neutral fat concentration in whole blood in each of Examples 5 and 6.

DESCRIPTION OF EMBODIMENTS

According to the invention, supplied is a biosensor comprising an insulating base plate, an electrode system containing at least a working electrode and a counter electrode and formed on the insulating base plate, and a sample-supplying section formed on the electrode system, wherein the sample-supplying section has a reaction layer including: a first reaction layer formed on the electrode system and containing at least a redox enzyme including, as a prosthetic group, pyrroloquinoline quinone (PQQ), flavin adenine dinucleotide (FAD), or flavin mononucleotide (FMN) (in the specification, the layer may be referred to merely as "first reaction layer"); and a second reaction layer formed by applying, onto the first reaction layer, a solution containing a lipid decomposing enzyme (in the specification, the layer may be referred to merely as "second reaction layer"). The invention is characterized in that the reaction layer is made into a bilayered structure including the redox-enzyme-containing first reaction layer and the lipid-decomposing-enzyme-containing second reaction layer, and, the second reaction layer is formed by applying a lipid-decomposing-enzyme-containing solution directly onto the first reaction layer.

As described above, reports have been hitherto made about biosensors: the above-mentioned two enzymes were mixed with each other to be made into a single layer in a biosensor as described in Patent Literature 1; and as described in Patent Literatures 2 and 3, in a biosensor, a bilayered layer structure having a polymer layer containing a redox enzyme and a water-soluble polymer, and a filter layer or nonwoven cloth layer laid on the polymer layer and composed of a carrier, such as a filter paper or nonwoven cloth, and a neutral enzyme decomposing enzyme is carried separately onto this carrier. In the case of the biosensor of Patent Literature 1 out of these biosensors, the redox enzyme, such as glycerol dehydrogenase (GLDH), is generally lower in solubility than the lipid decomposing enzyme. This matter affects onto the lipid decomposing enzyme; thus, reactions based on the two enzymes do not advance rapidly then the reaction rates are varied. It appears that these results in a delay of the enzyme reactions in the whole of sensor then the measuring period cannot be sufficiently shortened. In the case of the biosensors of Patent Literatures 2 and 3, since the lipid decomposing enzyme is separately carried on the filter paper or nonwoven cloth, the solubility of the redox enzyme is good. However, much time is required for causing a sample to penetrate into the polymer layer. It appears that this also results in a delay of the enzyme reactions in the whole of sensor then the measuring period cannot be sufficiently shortened.

Thereagainst, in the invention, a solution containing a lipid decomposing enzyme is applied onto the first reaction layer containing a redox enzyme to form the second reaction layer directly on the first reaction layer. Accordingly, when a sample containing fats, such as neutral fat, is passed through the sample-supplying section to be brought into contact with the lipid decomposing enzyme in the second reaction layer, this lipid decomposing enzyme is rapidly dissolved since the lipid decomposing enzyme is high in solubility. As a result, this enzyme decomposes the fats in the sample to generate free fatty acids, and glycerol. This reaction is completed within a required period equivalent to the period required for the completion of the dissolution of the lipid decomposing enzyme. Next, since the redox enzyme is present in the first reaction layer between the second reaction layer and the electrodes, after the completion of the dissolution of the lipid decomposing enzyme in the second reaction layer, the redox enzyme starts to dissolve. The sample in which the lipid was decomposed penetrates rapidly into the first reaction layer, the sample dissolves the redox enzyme, and the generated glycerol generates reduced-form electron carrier. The quantity of increase in the reduced-form electron carrier is then electrochemically measured. For this reason, according to the biosensor of the invention, fats in a sample can be quantitatively determined in a short period. The respective mechanisms in Patent Literatures 1 to 3, and the mechanism of the invention are based on inferences, and the invention is not limited by this mechanism.

Hereinafter, embodiments of the biosensor of the invention will be specifically described with reference to the drawings. The invention is not limited to the embodiments as far as possible embodiments do not depart from the scope of the claims. In the drawings, any dimension ratio may be exaggerated for the convenience of explanation to be different from actual ratio.

Figure 1:
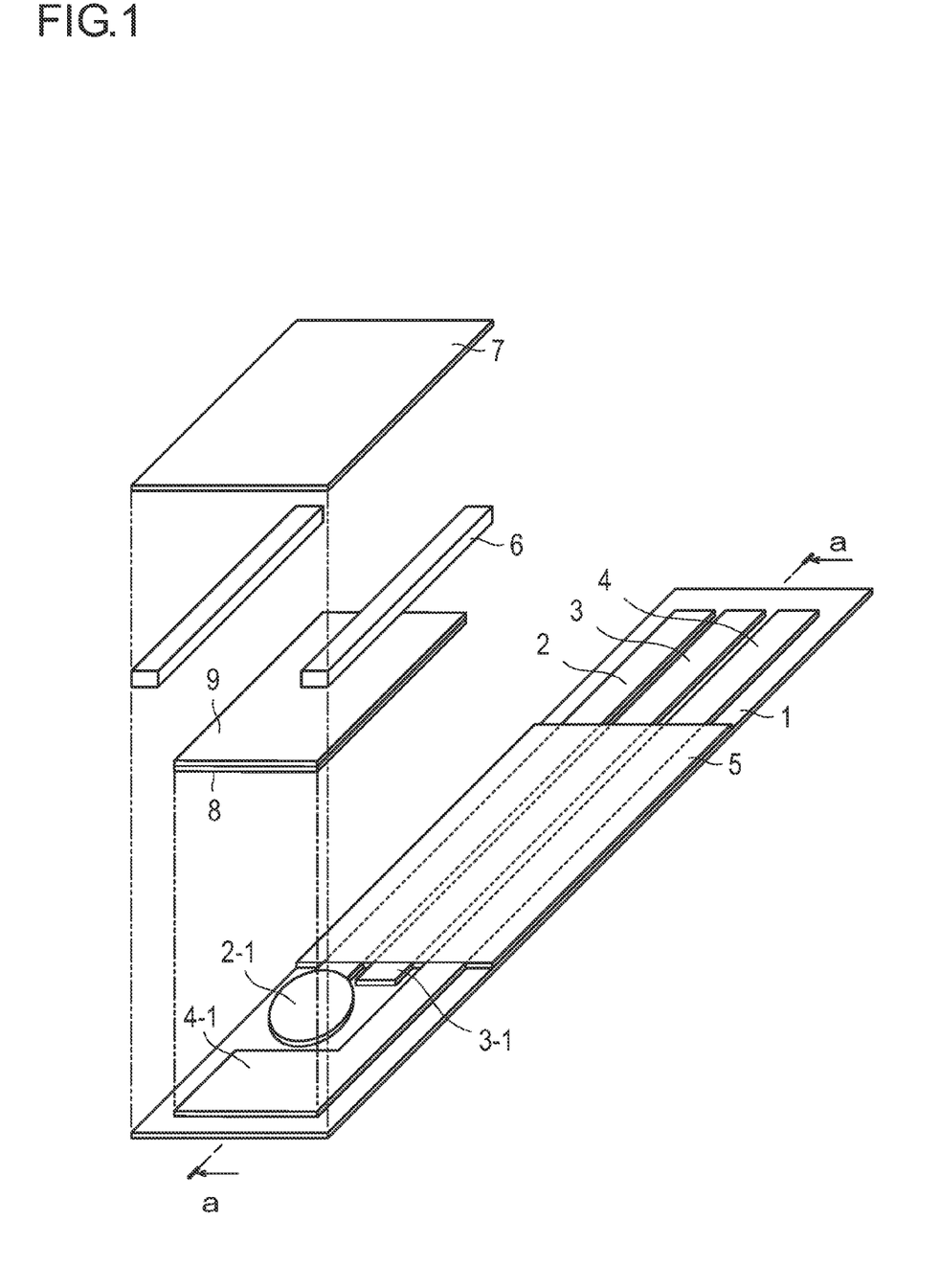
Figure 2:
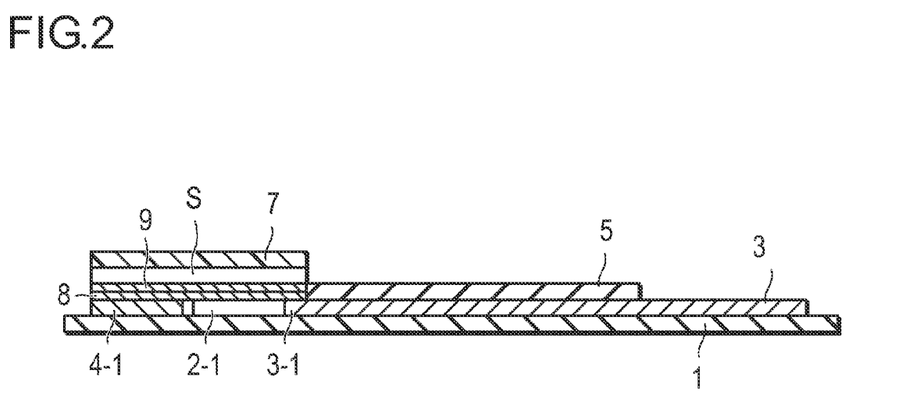

FIG. 1 is an exploded perspective view illustrating one of the embodiments of the biosensor of the invention. FIG. 2 is a sectional view of the biosensor in FIG. 1. In the present specification, the biosensor illustrated in FIGS. 1 and 2 may be referred to as a "first biosensor".

As illustrated in FIGS. 1 and 2, an electrode system including working electrode 2, reference electrode 3 and counter electrode 4 is formed on insulating base plate 1, which may be referred to merely as "base plate" in the specification. The electrode system needs to include at least a working electrode and a counter electrode. Thus, reference electrode 3 may be omitted. Layers of adhesive 6 are set on edges of the insulating base plate 1. The working electrode 2, the reference electrode 3 and the counter electrode 4 function as means for electrical connection of the biosensor. The working electrode 2, the reference electrode 3 and the counter electrode 4 may each be formed as an electrode having a desired pattern by appropriately referring to conventionally known findings, for example, about screen printing, sputtering or some other method, or by combining two or more thereof.

An insulating layer 5 is formed on the working electrode 2, the reference electrode 3 and the counter electrode 4 each formed on the insulating base plate 1 to make the electrode system exposed. The insulating layer 5 functions as an insulating means to prevent a short circuit between the individual electrodes. The method to form the insulating layer is not particularly limited. Thus, the layer may be formed by a conventionally known method such as a screen printing method or a bonding method.

Working region of working electrode 2-1, working region of reference electrode 3-1 and working region of counter electrode 4-1 are formed so as to sandwich insulating layer 5. On the working region of working electrode 2-1, the working region of reference electrode 3-1 and the working region of counter electrode 4-1, which constitute the electrode system, are successively formed first reaction layer 8 and second reaction layer 9. In FIG. 1, a sample-supplying section is composed of the first reaction layer 8, the second reaction layer 9, and space S positioned between the second reaction layer 9 and cover 7.

The first reaction layer 8 contains at least redox enzyme into which at least pyrroloquinoline quinone (PQQ), flavin adenine dinucleotide (FAD), or flavin mononucleotide (FMN) is incorporated as a prosthetic group (hereinafter, the redox enzyme may be referred to as the "redox enzyme in the invention").

The second reaction layer 9 is formed on the first reaction layer 8 and formed by applying at least a solution containing lipid decomposing enzyme thereonto. In the specification, "the second reaction layer is formed by applying a solution containing lipid decomposing enzyme" means that a solution containing a lipid decomposing enzyme is applied directly onto the first reaction layer, without carrying the lipid decomposing enzyme by a carrier such as a filter paper or a non-woven cloth, and then dried to form an applied film.

The working regions (2-1, 3-1 and 4-1) function as a potential applying means to apply an electric potential to a sample in the first reaction layer 8, and a current detecting means to detect a current flow in the sample when the biosensor is used. The working electrode 2, the reference electrode 3 and the counter electrode 4 including the working regions (2-1, 3-1 and 4-1), respectively, may be referred to as the working electrode 2, the reference electrode 3 and the counter electrode 4, respectively. The working electrode 2 and the counter electrode 4 work in the form of a pair when the biosensor is used, and function as a current measuring means to measure an oxidation current (response current) flowing when the potential is applied to the sample in the first reaction layer 8. When the biosensor is used, the reference electrode 3 is used as a reference base to apply a predetermined potential to the counter electrode 4 and the working electrode 2 across these electrodes.

The biosensor of the present embodiment is formed by bonding the cover 7 (onto the base plate 1) with the adhesive (double-sided tape) 6 laid on the base plate 1 to cover the first reaction layer 8 and the second reaction layer 9. The adhesive (double-sided tape) 6 may be laid on the electrode-side part, or only on the cover-7-side part, or may be laid on the both.

In the biosensor of the invention, it is preferred that the sample-supplying section further contains electron carrier. In this embodiment, the electron carrier may be present in any embodiment inside the sample-supplying section. Specific examples of the embodiments include a embodiment (A) that the first reaction layer 8 contains electron carrier (electron carrier is located in the first reaction layer 8); an embodiment (B) that the second reaction layer 9 contains electron carrier (electron carrier is located in the second reaction layer 9), and an embodiment (C) that a third reaction layer containing the electron carrier is further laid. Any one of these embodiments (A), (B) and (C) may be used, or two or more of the embodiments (A), (B) and (C) may be used in combination. Out of the embodiments, the embodiment (B) or (C) is more preferred. In other words, it is preferred about the biosensor of the invention that the second reaction layer has electron carrier (electron carrier is located in the second reaction layer), or the biosensor further has a third reaction layer containing electron carrier.

In the case of the former (the second reaction layer has electron carrier), it is preferred that a layer containing a surfactant, which may be referred to as surfactant layer hereinafter, is further located in the sample-supplying section to be separated from the first and second reaction layers 8 and 9. The arrangement of the surfactant layer is not particularly limited. Preferably, for example, the surfactant layer is formed on the cover side to be separated from the first and second reaction layer 8 and 9. When the surfactant layer is formed on the cover side in this case, the spread or wettability of a sample, such as whole-blood sample, onto the cover side is better than when the cover 7 directly contacts the sample. Thus, produced is an advantage that the sample can be speedily introduced into the sample-supplying section.

In the case of the latter (a third reaction layer has electron carrier), it is preferred that the third reaction layer, which has electron carrier, is further located in the sample-supplying section to be separated from the first and second reaction layers 8 and 9. The arrangement of the third reaction layer is not particularly limited. Preferably, for example, the third reaction layer is formed on the cover side to be separated from the first and second reaction layer 8 and 9. When the biosensor has electron carrier according to this arrangement, gained are advantageous effects that an improvement is made in the stability of the electron carrier itself, or the redox enzyme when the biosensor is stored. This is an advantageous effect based on the fact that the electron carrier and the redox enzyme do not contact each other.

In other words, a different embodiment of the biosensor of the invention in a case where the biosensor contains a third reaction layer is a biosensor including an insulating base plate, an electrode system containing at least a working electrode and a counter electrode and formed on the insulating base plate, and a sample-supplying section formed on the electrode system, wherein: the sample-supplying section has a reaction layer including a first reaction layer formed on the electrode system and containing at least a redox enzyme into which pyrroloquinoline quinone (PQQ), flavin adenine dinucleotide (FAD), or flavin mononucleotide (FMN) is incorporated as a prosthetic group; a second reaction layer formed by applying, onto the first reaction layer, a solution including a lipid decomposing enzyme; and further the third reaction layer containing an electron carrier is located to be separated from the first and second reaction layers. Hereinafter, the biosensor according to the different embodiment of the invention will be described with reference to FIGS. 3 and 4.

Figure 3:
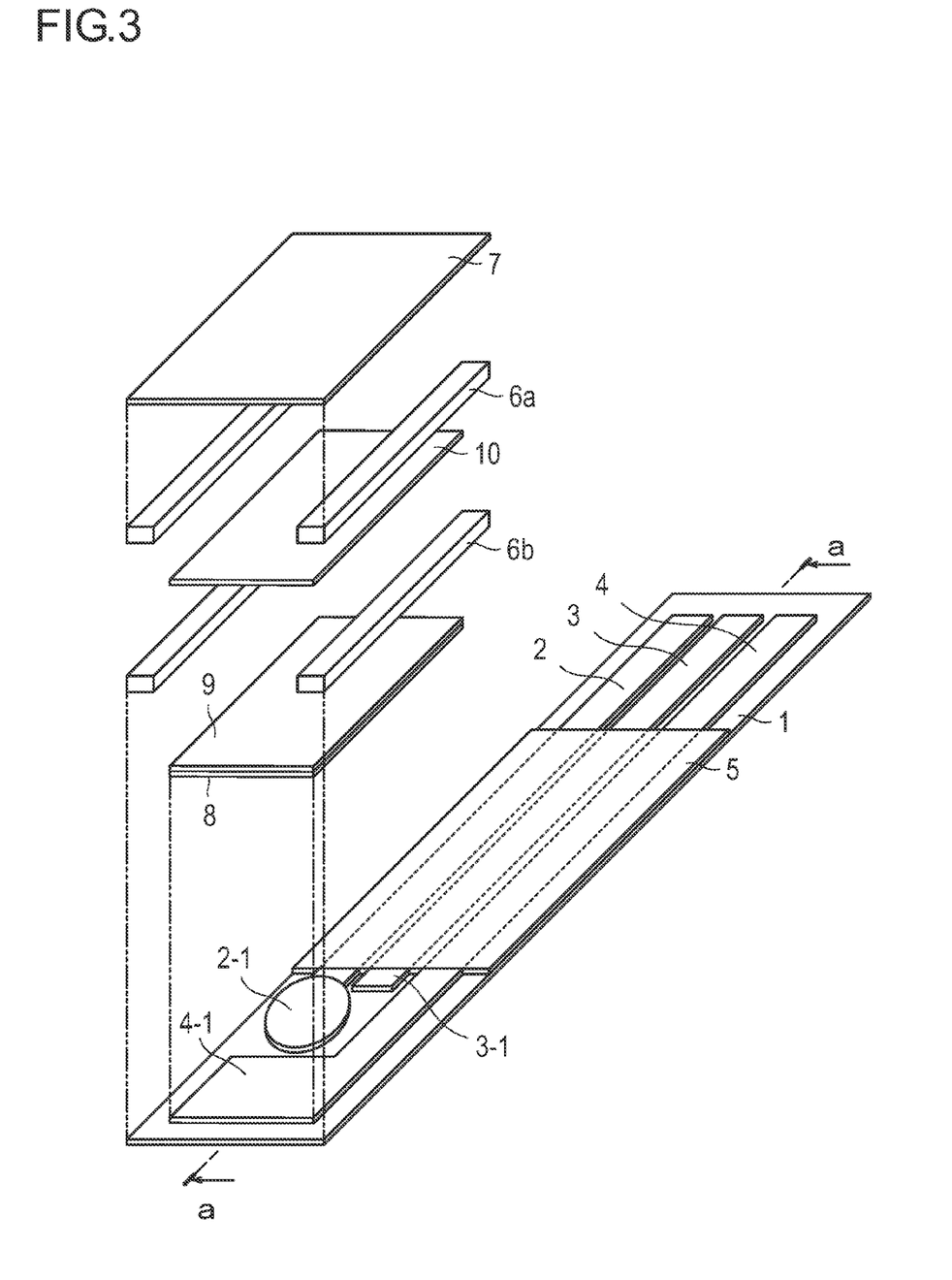
Figure 4:
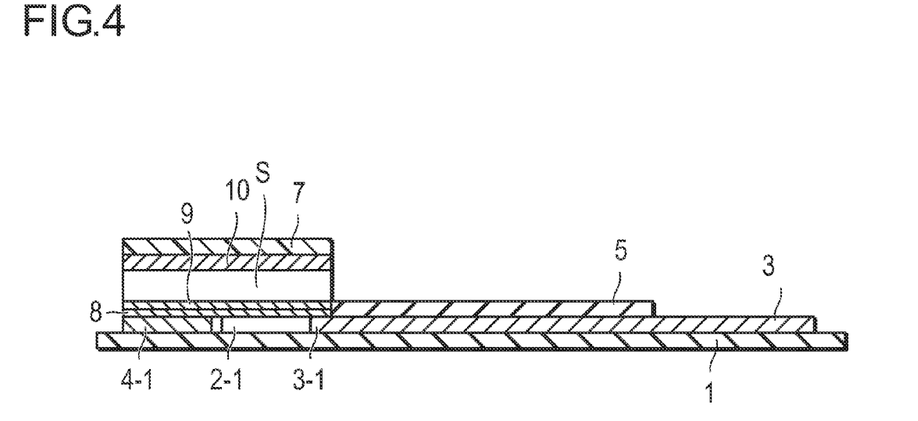

FIG. 3 is an exploded perspective view illustrating the different embodiment of the biosensor of the invention, which contains a third reaction layer. FIG. 4 is a sectional view of the biosensor in FIG. 3. In the specification, the biosensor illustrated in FIGS. 3 and 4 may be referred to as "second biosensor".

As illustrated in FIGS. 3 and 4, a basic structure thereof is identical with that of the biosensor illustrated in FIGS. 1 and 2 except that third reaction layer 10 containing electron carrier is further laid (specifically, third reaction layer 10 is located together with first reaction layer 8 and second reaction layer 9). In other words, a layer formed on cover 7 side is referred to as third reaction layer 10; and out of two layers formed on an electrode side part, a layer nearer to its electrodes and the other layer are referred to as first reaction layer 8 and second reaction layer 9, respectively. The sample-supplying section is composed of the first, second and third reaction layers 8, 9 and 10, and space S arranged between the second reaction layer 9 and the third reaction layer 10. The first reaction layer 8 contains redox enzyme, the second reaction layer 9 contains lipid decomposing enzyme, and the third reaction layer 10 contains electron carrier. In conclusion, in the second biosensor according to the different embodiment, it is unallowable that the redox enzyme, the lipid decomposing enzyme, and the electron carrier are simultaneously contained in the same reaction layer. The third reaction layer 10 is formed on the cover 7, which has two edges on which layers of adhesive (double-sided tape) 6a are located, respectively, to be arranged in a gap between the two edges.

The second biosensor is formed by bonding adhesives (double-sided tapes) 6b bonded to base plate 1 on which the first and second reaction layers 8 and 9 are formed, and, the adhesives (double-sided tapes) 6a bonded to the cover 7 on which the first reaction layer 8 is formed, together. The adhesive (double-sided tape) 6 may be located only on the base plate 1 side, or may be located only on the cover 7 side.

Hereinafter, the individual structural requirements will be detailed. As described above, the structure of the first biosensor is identical with that of the second biosensor except that the second biosensor further has the third reaction layer 10; thus, any specific description about the structural requirements described below is applicable to the first and the second biosensors of the invention unless otherwise specified. When the contained amount of each of the structural requirements is described, the term "per sensor" may be used. In the specification, the term "per sensor" means the following: for each sensor in which the volume of sample to be supplied to the sample-supplying section is "0.1 to 20 µl (preferably about 2 µl)", and the sensor size is the size of ordinary biosensors. Thus, about biosensors having a size smaller or larger than that size, the invention can be applied thereto by adjusting the contained amount of the each of the structural requirements appropriately.

<Insulating Base Plate>

The insulating base plate 1 used in the invention is not particularly limited; thus, a conventionally known material may be used therefor. Examples thereof include plastics, papers, glasses, and ceramics. The shape and the size of the insulating base plate 1 are not particularly limited.

The plastics are not particularly limited either, and may be conventional known ones. Examples thereof include polyethylene terephthalate (PET), polyesters, polystyrene, polypropylene, polycarbonates, polyimides, and acrylic resins.

<Electrodes>

The electrodes in the invention include at least the working electrode 2 and the counter electrode 4.

The electrodes in the invention are not particularly limited as far as the electrodes are capable of detecting a reaction of the sample (the target to be measured) and the redox enzyme in the invention electrochemically. Examples thereof include carbon electrode, gold electrode, silver electrode, platinum electrode, and palladium electrode. From the viewpoint of corrosion resistance and costs, carbon electrodes are preferred.

In the invention, the electrodes may be of a two-electrode type, which includes only the working electrode 2 and the counter electrode 4, or may be of a three-electrode type, which further includes the reference electrode 3. The three-electrode type may be more preferably used than the two-electrode type in order to attain potential-control with a higher sensitivity. The electrodes in the invention may include ther electrode such as a detecting electrode to detect the quantity of a liquid.

A region thereof which contacts the sample-supplying section (working region) may be made of a constituting material different from that of the other electrode regions. When the reference electrode 3 is made of, for example, carbon, working region of reference electrode 3-1 may be made of silver/silver chloride. Since ordinary biosensors are disposable, it is advisable to use disposable electrodes as the electrodes.

<Insulating Layer>

Material constituting insulating layer 5 is not particularly limited, and examples thereof include resist ink, resins such as PET and polyethylene, glass, ceramic, and paper. The material is preferably PET.

<Sample-Supplying Section>

As described above, in the first biosensor of the invention, the sample-supplying section has the first reaction layer 8, which contains redox enzyme, and the second reaction layer 9, which contains lipid decomposing enzyme. When the surfactant layer is laid on the cover-7-side to be separated from the first and second reaction layers, the sample-supplying section also has the surfactant layer.

In the second biosensor of the invention, the sample-supplying section has not only the first reaction layer 8, which contains redox enzyme, and the second reaction layer 9, which contains lipid decomposing enzyme, but also the third reaction layer 10, which is formed separately from the first and second reaction layers 8 and 9, and the third reaction layer 9 contains electron carrier. By providing a third reaction layer as in the second biosensor of the invention, the redox enzyme and the electron carrier can be included indifferent layers from each other, then, the biosensor can be prevented from being deteriorated by contact between the electron carrier and the redox enzyme when stored.

In the invention, the respective thicknesses of the first and second reaction layers 8 and 9 are not particularly limited, and may each be appropriately selected to be a thickness of ordinary reaction layers. The thickness of the first reaction layer 8 is preferably from 0.01 to 25 µl, more preferably from 0.025 to 10 µm, in particular preferably from 0.05 to 8 µm. The thickness of the second reaction layer 9 is preferably from 0.01 to 25 µm, more preferably from 0.025 to 10 µm, in particular preferably from 0.05 to 8 µm. It is advisable to set the total thickness of the first and second reaction layers 8 and 9 to be within a range preferably from 0.02 to 50 µm, more preferably from 0.05 to 20 µm, in particular preferably from 0.1 to 16 µm. The method to control each of the thicknesses is not particularly limited. For example, the thickness can be controlled by adjusting appropriately the application quantity (for example, the dropping quantity) of the solution containing predetermined components.

When the surfactant layer is formed on the cover 7 side to be separated from the first and second reaction layers 8 and 9 in the first biosensor of the invention, the thickness thereof is preferably from 0.01 to 25 µm, more preferably from 0.025 to 10 µm, even more preferably from 0.05 to 8 µm. The separation distance between the second reaction layer 9 and the surfactant layer is preferably from 0.05 to 1.5 mm, more preferably from 0.07 to 1.25 mm, even more preferably from 0.09 to 1 mm. When the distance is in this range, a capillary phenomenon is easily caused then a sample is easily introduced into the sample-supplying section. The thicknesses of the first and second reaction layers 8 and 9, and the optionally formed surfactant layer may be the same or different.

In the second biosensor of the invention, the respective thicknesses of the first and second reaction layers 8 and 9 and the third reaction layer are not particularly limited, and may each be appropriately selected to be an ordinary reaction layer thickness. The thickness of the first reaction layer 8 is preferably from 0.01 to 25 µm, more preferably from 0.025 to 10 µm, in particular preferably from 0.05 to 8 µm. The thickness of the second reaction layer 9 is preferably from 0.01 to 25 µm, more preferably from 0.025 to 10 µm, in particular preferably from 0.05 to 8 µm. It is advisable to set the total thickness of the first and second reaction layers 8 and 9 in a range preferably from 0.02 to 50 µm, more preferably from 0.05 to 20 µm, in particular preferably from 0.1 to 16 µm.

It is advisable to set the thickness of the third reaction layer 10 to be within a range of preferably 0.01 to 10 µm, more preferably 0.025 to 10 µm, in particular preferably 0.05 to 8 µm. The respective thicknesses of the first, second and third reaction layers 8, 9 and 10 may be the same or different. The method to control each of the thicknesses is not particularly limited. For example, the thickness can be controlled by adjusting appropriately the application quantity (for example, the dropping quantity) of a solution containing predetermined components. The separation distance between the second reaction layer 9 and the third reaction layer 10 is not particularly limited, and is preferably from 0.05 to 1.5 mm, more preferably from 0.075 to 1.25 mm, in particular preferably from 0.1 to 1 mm. When the distance is in this range, the redox enzyme and the electron carrier do not contact each other when the biosensor is stored, and further a capillary phenomenon is easily caused then a sample is easily absorbed to the reaction layers. The separation distance can be controlled by controlling the thickness of the adhesive. In other words, the adhesive also fulfills function of a spacer to separate the second reaction layer 9 and the third reaction layer 10 from each other.

(Redox Enzyme)

In the invention, the first reaction layer 8 contains redox enzyme into which pyrroloquinoline quinone (PQQ), flavin adenine dinucleotide (FAD), or flavin mononucleotide (FMN) is incorporated as a prosthetic group, which may be referred to as "coenzyme". The redox enzyme is in particular preferably a polyol dehydrogenase into which pyrroloquinoline quinone (PQQ) is incorporated as a prosthetic group. About the redox enzyme in the invention, only one species thereof may be used, or two or more species thereof may be used in a mixture form.

In the invention, the redox enzyme, into which pyrroloquinoline quinone (PQQ), flavin adenine dinucleotide (FAD), or flavin mononucleotide (FMN) is incorporated as a prosthetic group, is not particularly limited, and is dependent on the kind of the sample. Examples of the redox enzyme into which pyrroloquinoline quinone (PQQ) is incorporated as a prosthetic group include glycerol dehydrogenase, sorbitol dehydrogenase, mannitol dehydrogenase, arabitol dehydrogenase, galactitol dehydrogenase, xylitol dehydrogenase, adonitol dehydrogenase, erythritol dehydrogenase, ribitol dehydrogenase, propylene glycol dehydrogenase, fructose dehydrogenase, glucose dehydrogenase, gluconic acid dehydrogenase, 2-ketogluconic acid dehydrogenase, 5 ketogluconic acid dehydrogenase, 2,5-diketogluconic acid dehydrogenase, alcohol dehydrogenase, cyclic alcohol dehydrogenase, acetoaldehyde dehydrogenase, amine dehydrogenase, shikimic acid dehydrogenase, and galactose oxidase.

Examples of the redox enzyme into which flavin adenine dinucleotide (FAD) or flavin mononucleotide (FMN) is incorporated as a prosthetic group include glucose oxidase, glucose dehydrogenase, D-amino acid oxidase, succinic acid dehydrogenase, monoamine oxidase, sarcosine dehydrogenase, glycerol dehydrogenase, sorbitol dehydrogenase, D-lactic acid dehydrogenase, and cholesterol oxidase.

Preferred is glycerol dehydrogenase into which at least one of pyrroloquinoline quinone (PQQ) or flavin adenine dinucleotide (FAD) is incorporated as a prosthetic group, and particularly preferred is glycerol dehydrogenase into which pyrroloquinoline quinone (PQQ) is incorporated as a prosthetic group (hereinafter, this combination may be referred to as "PQQ-dependent glycerol dehydrogenase").

The redox enzyme in the invention may be a purchased commercially available product, or an enzyme prepared in person. The method for preparing the redox enzyme in person may be, for example, a known method of cultivating bacteria which can produce the redox enzyme in a nutrient medium, and then extracting the redox enzyme from the culture (see, for example, JP-A No. 2008-220367).

In the case of, for example, PQQ-dependent glycerol dehydrogenase, a specific example of bacteria which can produce the glycerol dehydrogenase includes bacteria belonging to various genera, such as Gluconobacter and Pseudomonas. It is particularly preferred to use PQQ-dependent glycerol dehydrogenase that is present in a membrane fraction of bacteria belonging to Gluconobacter. In particular, the following can be used from the viewpoint of easiness in availability: Gluconobacter albidus NBRC 3250, 3273, 103509, 103510, 103516, 103520, 103521, or 103524; Gluconobacter cerinus NBRC 3267, 3274, 3275, or 3276; Gluconobacter frateurii NBRC 3171, 3251, 3253, 3262, 3264, 3265, 3268, 3270, 3285, 3286, 3290, 16669, 103413, 103421, 103427, 103428, 103429, 103437, 103438, 103439, 103440, 103441, 103446, 103453, 103454, 103456, 103457, 103458, 103459, 103461, 103462, 103465, 103466, 103467, 103468, 103469, 103470, 103471, 103472, 103473, 103474, 103475, 103476, 013477, 103482, 103487, 103488, 103490, 103491, 103493, 103494, 103499, 103500, 103501, 103502, 103503, 103504, 103506, 103507, 103515, 103517, 103518, 103519, or 103523; Gluconobacter japonicus NBRC 3260, 3263, 3269, 3271 or 3272; Gluconobacter kanchanaburiensis NBRC 103587, or 103588; Gluconobacter kondonii NBRC 3266; Gluconobacter oxydans NBRC 3130, 3189, 3244, 3287, 3292, 3293, 3294, 3462, 12528, or 14819; Gluconobacter roseus NBRC 3990; Gluconobacter sp NBRC 3259, or 103508; Gluconobacter sphaericus NBRC 12467; Gluconobacter thailandicus NBRC 3172, 3254, 3255, 3256, 3257, 3258, 3289, 3291, 100600, or 100601.

The medium for cultivating PQQ-dependent glycerol dehydrogenase may be a synthetic medium or a natural medium as far as the medium contains appropriate quantities of a carbon source, a nitrogen source, an inorganic substance and other necessary nutrients that can be utilized by a bacterial strain used. Usable examples of the carbon source include glucose, glycerol, and sorbitol. Usable examples of the nitrogen source include nitrogen-containing natural products such as peptones, meat extracts and yeast extracts; and nitrogen-containing inorganic substances such as ammonium chloride, and ammonium citrate. Usable examples of the inorganic substances include potassium phosphate, sodium phosphate, and magnesium sulfate. Additionally, specific vitamins may be optionally used. The above-mentioned carbon sources, as well as the nitrogen sources, the inorganic substances, or other necessary nutrients, may be used alone or in combination of two or more thereof.

The cultivation is preferably shaking cultivation, or aerated mixing cultivation. The cultivating temperature is preferably 20 to 50° C., more preferably 22 to 40° C., most preferably 25 to 35° C. The cultivating pH is preferably 4 to 9, more preferably 5 to 8. Conditions other than these conditions are permissible as far as the bacterial strain used grows. Usually, the cultivation period is preferably 0.5 to 5 days. By the cultivation, a redox enzyme is accumulated in bacterial cells. The redox enzyme may be an enzyme obtained by the cultivation, or a recombinant enzyme obtained by transducing genes of the redox enzyme into colon bacillus or other bacteria.

Next, the resultant PQQ-dependent glycerol dehydrogenase is extracted. The method for the extraction may be an ordinarily used extracting method, examples of which include an ultrasonic fracturing method, a French pressing method, an organic solvent method, and a lysozyme method. The method to purify the extracted redox enzyme is not particularly limited, and may be, for example, a salting-out method with ammonium sulfate, mirabilite or some other material; a metal aggregating method using magnesium chloride or calcium chloride; nucleic acid removal using streptomycin or polyethyleneimine; or an ion exchange chromatographic method through DEAE (diethylaminoethyl)-sepharose, CM (carboxymethyl)-sepharose, or some other.

A partially purified enzyme or purified enzyme liquid yielded by such a method may be used as it is, or may be used in a chemically modified form. When the chemically modified redox enzyme is used in the invention, a redox enzyme obtained by the above-mentioned method, which originates from a cultivated product, is appropriately modified chemically by a method descried in, for example, JP-A No. 2006-271257 and the resultant may be used. The method for the chemical modification is not limited to the method described in this publication.

The contained amount of the redox enzyme in the invention is not particularly limited, and may be appropriately selected in accordance with the kind and the added amount of a sample to be measured, the kind of the electron carrier, the quantity of a water-soluble polymer that will be described later, and others. In the case of using, for example, PQQ-dependent glycerol dehydrogenase, the contained amount is preferably 0.01 to 100 U, more preferably 0.05 to 50 U, in particular preferably 0.1 to 10 U per sensor from the viewpoint of the enzyme amount (enzymatic activity amount) to decompose glycerol rapidly and not to lower the solubility of the reaction layers. The definition of the activity unit (U) of PQQ-dependent glycerol dehydrogenase, and the method for measuring the unit are according to a method described in JP-A No. 2006-271257. The redox enzyme containing PQQ-dependent glycerol dehydrogenase is preferably prepared by use of a buffer solution, such as glycylglycine, this matter being to be also described later.

(Lipid Decomposing Enzyme)

The second reaction layer 9 in the invention contains lipid decomposing enzyme which hydrolyzes ester bond which constitutes lipid. Therefore, the biosensor of the invention can be used as a neutral fat sensor. The lipid decomposing enzyme is not particularly limited, and specific examples thereof include lipoprotein lipase (LPL), lipase, and esterase. From the viewpoint of reactivity, lipoprotein lipase (LPL) is particularly preferred.

The contained amount of LPL is not particularly limited, and may be appropriately selected in accordance with the kind and the added amount of sample to be measured, the amount of hydrophilic polymer to be used, the kind of electron carrier, and others. The amount is preferably from 0.1 to 1000 activity unit (U), more preferably from 1 to 500 U, in particular preferably from 10 to 100 U from the viewpoint of, for example, the enzyme amount (enzymatic activity amount) to decompose neutral fat rapidly and not to lower the solubility of the reaction layers. The definition of the activity unit (U) of LPL, and the method for measuring the unit are according to the pamphlet of WO 2006/104077. LPL is preferably prepared by use of a buffer solution, such as glycylglycine, this matter being to be also described later.

In the invention, the oxidase and the lipid decomposing enzyme as each described above are each independently present in different layers of the first and second reaction layers. According to this embodiment, hydrolysis reaction by lipid decomposing enzyme advances efficiently.

(Electron Carrier)

The biosensor of the invention preferably contains an electron carrier. The electron carrier may be contained in the first or second reaction layer 8 or 9. Preferably, in the third reaction layer, which is separated from these reaction layers, the electron carrier is contained. In this case, the reaction layer containing the electron carrier is more preferably present separately from the electrodes, and is in particular preferably present separately from the first or second reaction layer 8 or 9, especially, the second reaction layer 9. In conclusion, the invention provides a biosensor (second biosensor) comprising an insulating base plate, an electrode system containing at least a working electrode and a counter electrode and formed on the insulating base plate, and a sample-supplying section formed on the electrode system, wherein, the sample-supplying section has reaction layers including a first reaction layer formed on the electrode system and containing at least a redox enzyme into which pyrroloquinoline quinone (PQQ), flavin adenine dinucleotide (FAD), or flavin mononucleotide (FMN) is incorporated as a prosthetic group, and a second reaction layer formed by applying, onto the first reaction layer, a solution including a lipid decomposing enzyme, and a third reaction layer containing an electron carrier is formed so as to be separated from the first and second reaction layers.

In the second biosensor of the invention, the third reaction layer 10 contains electron carrier, which may be referred to as "electron receptor". When the electron carrier is present separately from the electrodes as described herein, it is possible to restrain or prevent a phenomenon that the electron carrier is automatically reduced, as in a local battery. In this way, a biosensor having improved precision can be provided.

When the biosensor is used, the electron carrier receives electron generated by the effect of the redox enzyme, that is, the carrier is reduced. After the enzyme reaction ends, the reduced electron carrier is electrochemically oxidized by applying a potential to the electrodes. From the intensity of the current flowing at this time, which may be referred to as the "oxidation current" hereinafter, the concentration of the desired component in the sample can be calculated out.

The electron carrier used in the invention may be conventionally known one. The species thereof may be appropriately selected in accordance with the sample, and the redox enzyme used. About the electron carrier, one species thereof may be used, or two or more species thereof may be used in combination.

Preferably usable examples of the electron carrier are, more specifically, potassium ferricyanide, sodium ferricyanide, ferrocene and derivatives thereof, phenazine methosulfate and derivatives thereof, p-benzoquinone and derivatives thereof, 2,6-dichlorophenolindophenol, methylene blue, nitrotetrazolium blue, osmium complexes, and ruthenium complexes such as hexaammineruthenium (III) chloride. Of these examples, hexaammineruthenium (III) chloride and potassium ferricyanide are preferred, and hexaammineruthenium (III) chloride is more preferred.

The contained amount of the electron carrier is not particularly limited, and may be appropriately adjusted in accordance with the addition amount of the sample, and others. For example, in order to incorporate a sufficient amount of the electron carrier with respect to the substrate amount, the contained amount of the electron carrier is preferably from 1 to 2000 µg, more preferably from 5 to 1000 µg, in particular preferably from 10 to 500 µg per sensor. The electron carrier is preferably prepared by use of a buffer solution, such as glycylglycine, this will be also described later.

(Surfactant)

In the biosensor of the invention, the first, the second or the third layer 8, 9 or 10 contains a surfactant if necessary. In the first biosensor of the invention, a surfactant layer may be formed in the cover 7 side to be separated from the first and second reaction layers 8 and 9.

Any redox enzyme is made of a protein; thus, when the enzyme adheres onto the front surface of an electrode, the electrode front surface may be unfavorably passivated. Therefore, conventional ordinary biosensors have had a structure wherein an enzyme didn't directly contact their electrodes. However, when a surfactant is included in the first reaction layer 8, the redox enzyme is significantly restrained or prevented from adhering or fixing onto the electrodes. As a result, near the electrodes, the efficiency of the conversion of the electron carrier from the oxidized-form to the reduced-form by the redox enzyme can be improved. That is, higher the correlation with the substrate concentration in the sample liquid can be achieved. When the surfactant is formed in the cover 7 side, the spread or the wettability of a sample, such as a whole-blood sample, to the cover side is better than when the cover 7 directly contacts the sample. Thus, the sample can be introduced speedily into the sample-supplying section then that is favorable.

The surfactant used in the invention is not particularly limited as far as the surfactant does not lower the enzymatic activity of the redox enzyme in the invention to be used. A surfactant selected appropriately from the following may be used: for example, nonionic surfactants, amphoteric surfactants, cationic surfactants, anionic surfactant, and natural surfactants. These may be used alone or in a mixture form. The surfactant to be used is preferably at least one of a nonionic surfactant and an amphoteric surfactant in order not to adversely affect onto the enzymatic activity of the redox enzyme in the invention.

The nonionic surfactants are not particularly limited, and are preferably polyoxyethylene or alkylglycoside surfactants in order not to adversely affect onto the enzymatic activity of the redox enzyme in the invention.

The polyoxyethylene nonionic surfactants are not particularly limited, and are preferably polyoxyethylene-p-t-octylphenol (the number of oxyethylene=9, 10) [Triton (registered trademark) X-100], polyoxyethylene sorbitan monolaurate [Tween 20], polyoxyethylene sorbitan monopalmitate [Tween 40], polyoxyethylene sorbitan monostearate [Tween 60], polyoxyethylene sorbitan monooleate [Tween 80], polyoxyethylene polyoxypropylene glycol [Emalgen PP-290 (manufactured by Kao Corp.)], and others. Of these surfactants, preferred are polyoxyethylene-p-t-octylphenol (the number of oxyethylene=9, 10) [Triton (registered trademark) X-100], and polyoxyethylene polyoxypropylene glycol [Emalgen PP-290 (manufactured by Kao Corp.)] from the viewpoint of improving solubility of the redox enzyme of the invention.

The alkylglycoside nonionic surfactants are not particularly limited, and are preferably alkylglycosides and alkylthioglycosides each having an alkyl group having 7 to 12 carbon atoms, and others. The number of the carbon atoms is more preferably from 7 to 10, in particular preferably 8. Their saccharide moiety is preferably glucose, or maltose, more preferably glucose. More specifically, the saccharides are preferably n-octyl-β-D-glucoside, and n-octyl-β-D-thioglucoside. When the alkylglycoside nonionic surfactants are each used in the biosensor, the surfactant is very easily applied in manufacturing process then the applied surfactant can be even. In particular, n-octyl-β-D-thioglucoside is included in the reaction layer 10 (the first reaction layer 8, or the second reaction layer 9), a sample solution spreads very well when dropped thereon, and has a good wettability thereon (surface tension is not easily generated). Thus, from the viewpoint of the spread and wettability, alkylthioglycosides are far preferable than alkylglycosides. These may be used alone or in a mixture form.

The amphoteric surfactants are not particularly limited, and examples thereof include
3-[(3-cholamidopropyl)dimethylammonio]-1-propanesulfonic acid (CHAPS),
3-[(3-cholamidopropyl)dimethylammonio]-2-hydroxypropanesulfonic acid (CHAPSO), and
n-alkyl-N—N-dimethyl-3-ammonio-1-propanesulfonic acid (Zwittergent (registered trademark)). These may be used alone or in a mixture form. Preferred is
3-[(3-cholamidopropyl)dimethylammonio]-1-propanesulfonic acid (CHAPS), or
3-[(3-cholamidopropyl)dimethylammonio]-2-hydroxypropanesulfonic acid (CHAPSO). Particularly preferred is CHAPS since hemolysis by CHAPS is lower among surfactants.

The cationic surfactants are not particularly limited, and examples thereof include cetylpyridinium chloride, and trimethylammonium bromide. These may be used alone or in a mixture form.

The anionic surfactants are not particularly limited, and examples thereof include sodium cholate, and sodium deoxycholate. These may be used alone or in a mixture form.

The natural surfactants are not particularly limited, and examples thereof include phospholipids. Preferred examples thereof include lecithins such as egg yolk lecithin, soybean lecithin, hydrogenated lecithin, high-purity lecithin. These may be used alone or in a mixture form.

When a whole-blood sample is used as a sample, it is preferred, from the viewpoint of a further improvement in the precision of the biosensor, to use a surfactant which is low hemolytic among the surfactants. Specific and preferred examples thereof include above-mentioned CHAPS, Tween, and Emalgen PP-290 (polyoxyethylene polyoxypropylene glycol, manufactured by Kao Corp.).

In the second biosensor of the invention, such a surfactant may be included in any one of the first, second and third reaction layers 8, 9 and 10, or is included preferably in the first or third reaction layer 8 or 10, more preferably in the first and third reaction layers 8 and 10. Thereby, the dissolution of the redox enzyme or the electron carrier may be promoted. When the surfactant is present in two or more of the three reaction layers, respective species and their amounts of the surfactant that are included in these reaction layers may be the same or different. It is preferred to select the species or amounts, considering interaction with each of the structural requirements contained in each of the first, second and third reaction layers 8, 9 and 10.

More specifically, as described above, the redox enzyme is included in the first reaction layer 8. In the case of including, for example, PQQ-dependent glycerol dehydrogenase as the redox enzyme, it is preferred to include the surfactant at least in the first reaction layer 8 because the enzyme has high hydrophobicity. In this case, in order to improve the biosensor further in precision when a whole-blood sample is used as a sample, it is preferred to use, as the species of the surfactant, a low hemolytic surfactant (for example, CHAPS, Tween, Emalgen PP-290, or others). Meanwhile, as described above, in the second biosensor, the third reaction layer 10 contains the electron carrier (for example, hexaammineruthenium (III) chloride); in order to improve the spread and the wettability to further improve precision of the biosensor, it is more preferred to make the surfactant be included in the third reaction layer 10 also. In this case also, it is preferred to use a low hemolytic surfactant (for example, CHAPS, Tween, Emalgen PP-290, or others) taking account of the spread and the wettability. Thereby, the biosensor is further improved in precision.

The contained amount of the surfactant is not particularly limited, and may be appropriately adjusted in accordance with the added amount of the sample, and others.

When an amphoteric surfactant is used, the contained amount is preferably from 0.01 to 100 μg, more preferably from 0.05 to 50 μg, in particular preferably from 0.1 to 10 μg per sensor in order to raise solubility of the redox enzyme in the invention, prevent inactivation of the enzyme, and apply the surfactant easily in the production process. The surfactant is also preferably prepared by use of a buffer solution, such as glycylglycine, this will be also described later. When two or more species of the surfactant are contained per sensor, the contained amount means the total amount thereof.

When a nonionic surfactant is used as the surfactant, the contained amount is preferably from 0.01 to 100 μg, more preferably from 0.05 to 50 μg, in particular preferably from 0.1 to 10 μg per sensor in order to raise solubility of the redox enzyme in the invention, prevent inactivation of the enzyme, and apply the surfactant easily in the production process. The surfactant is preferably prepared by use of a buffer solution, such as glycylglycine.

(Hydrophilic Polymer)

In the invention, the first, second or third reaction layer 8, 9 or 10 may further contain a hydrophilic polymer.

As described above, any redox enzyme is made of a protein; thus, when the enzyme adheres onto the front surface of electrode, the electrode front surface may be unfavorably passivated. Therefore, conventional ordinary biosensors had a structure wherein an enzyme didn't directly contact their electrodes. However, when the hydrophilic polymer is included in the first reaction layer 8, the redox enzyme is significantly restrained or prevented from adhering or fixing onto the electrodes. Near the electrodes, the efficiency of conversion of the electron carrier from oxidized-form to reduced-form by the redox enzyme can be improved. That is, the correlation with the substrate concentration in the sample liquid is enhanced.

In the case of the first biosensor, the hydrophilic polymer may be contained in either the first or second reaction layer 8 or 9. In the case of the second biosensor, the hydrophilic polymer may be contained in either the first, second or third reaction layer 8, 9 or 10. The hydrophilic polymer has a function of immobilizing the redox enzyme or the electron carrier in the invention onto the electrodes. Thus, when the first, second or third reaction layer 8, 9 or 10, in particular, the first or third reaction layer 8 or 10 contains the hydrophilic polymer, these reaction layers can be prevented from being peeled from the surfaces of the base plate 1 and the electrodes. The hydrophilic polymer also has an advantageous effect of preventing the respective surfaces of the first, second and third reaction layers 8, 9 and 10 from being cracked. Thus, the hydrophilic polymer is advantageous to improve the biosensor in reliability. Furthermore, the hydrophilic polymer also can restrain adsorbable components, such as proteins, from being adsorbed onto the electrodes. When the first, second or third reaction layer 8, 9 or 10 contains the hydrophilic polymer, the biosensor may be in the form that the hydrophilic polymer is contained in the reaction layer, or in the form that a hydrophilic polymer layer containing the hydrophilic polymer is formed to cover the first, second or third reaction layer 8, 9 or 10.

The hydrophilic polymer usable in the invention may be conventionally known one. More specific examples of the hydrophilic polymer include polyethylene glycol, carboxymethylcellulose, hydroxyethylcellulose, hydroxypropylcellulose, methylcellulose, ethylcellulose, ethylhydroxyethylcellulose, carboxymethylethylcellulose, polyvinylpyrrolidone, polyvinyl alcohol, polyamino acids such as polylysine, polystyrenesulfonic acid, gelatin and derivatives thereof, acrylic acid polymers or derivatives thereof, polymers of maleic anhydride or salts thereof, and starch and derivatives thereof. Of these polymers, preferred are carboxymethylcellulose, polyvinylpyrrolidone, polyethylene glycol, and polyvinyl alcohol since the enzymatic activity of the redox enzyme in the invention is not lost, and further these have high solubility. These may be used alone or in a mixture form.

The mixed amount of such a hydrophilic polymer is preferably from 0.01 to 100 µg, more preferably from 0.05 to 50 µg, in particular preferably from 0.1 to 10 µg per sensor in order to immobilize the enzyme or the electron carrier and prevent decline of solubility of the reaction layers. The hydrophilic polymer is also preferably prepared by use of a buffer solution, such as glycylglycine, this will be also described later. When the hydrophilic polymer is present in two or more of the first, second and third reaction layers 8, 9 and 10, respective species and mixed amounts of the hydrophilic polymer that are included in these reaction layers may be the same or different. It is preferred to select the species or amounts by considering interaction with each of the structural requirements contained in each of the first, second and third reaction layers 8, 9 and 10.

(Saccharide)

In the first and second biosensors of the invention, at least one of the first, second and third reaction layers 8, 9 and 10 may further contain a saccharide. The saccharide may be appropriately selected from saccharides that are not involved in enzyme reaction related to the measurement, and do not react in themselves, and used. The saccharide can contribute to the immobilization or stabilization of the individual layer(s). The saccharide may be contained in any one of the first, second and third reaction layers 8, 9 and 10, and is preferably contained at least in the first reaction layer 8.

The saccharide, which may be contained in at least one of the first, second and third reaction layers 8, 9 and 10, is preferably a non-reducing saccharide, which neither has a free aldehyde nor a free ketone group to have no reducibility. Examples of the non-reducing saccharide include trehalose type oligosaccharides, in each of which reducing groups are bonded to each other, glycosides, in each of which a reduced-form group of saccharide is bonded to a non-saccharide compound, and saccharide alcohols, in each of which a saccharide has been hydrogenated and reduced. More specific examples thereof include trehalose type oligosaccharides such as sucrose, trehalose, and raffinose; glycosides such as alkylglycoside, phenol glycoside, and mustard seed oil glycoside; and saccharide alcohols such as arabitol, and xylitol. These non-reducing saccharides may be used alone or in the form of a mixture of two or more thereof. Of these saccharides, preferred are trehalose, raffinose and sucrose, and in particular referred is trehalose.

The mixed amount of the saccharide, which is contained in at least one of the first, second and third 8, 9 and 10, is preferably from 0.1 to 500 µg, more preferably from 0.5 to 400 µg, even more preferably from 1 to 300 µg per sensor. When the saccharide is in a mixture form, the mixed amount means the total amount of all saccharides. When the mixed amount is in the range, the saccharide contributes to the immobilization or stabilization of the individual layers without lowering the performance of sensor.

(Protein)

In the first and second biosensors of the invention, at least one of the first, second and third reaction layers 8, 9 and 10 may further contain a protein. The protein may be appropriately selected from proteins that are not involved in enzyme reaction related to the measurement and do not react themselves nor exhibit any physiological activity, and used. The protein can contribute to the immobilization or stabilization of the individual layers. The protein may be contained in anyone of the first, second and third reaction layers 8, 9 and 10, and is preferably contained at least in the first reaction layer 8.

Examples of the protein, which may be contained in at least one of the first, second and third reaction layers 8, 9 and 10, include bovine serum albumin (BSA), casein, sericin, and hydrolysates thereof. These proteins may be used alone or in the form of a mixture of two or more thereof. Of these proteins, BSA is preferred because the protein is easily available and is low in costs. The molecular weight of the protein is preferably from 10 to 1000 kDa, more preferably from 25 to 500 kDa, even more preferably from 50 to 100 kDa. The molecular weight adopted here is a value measured by use of gel permeation chromatography.

The mixed amount of the protein contained in the first, second and third reaction layers 8, 9 and 10 is preferably from 0.1 to 200 µg, more preferably from 0.5 to 100 µg, even more preferably from 1 to 50 µg per sensor. When the protein is in the form of a mixture of two or more species thereof, the mixed amount means the total amount of all species. When the mixed amount is within the range, the protein contributes to the immobilization or stabilization of the individual layers without lowering the performance of biosensor.

<Method for Producing Biosensor>

The method to form the first, second and third reaction layers 8, 9 and 10 in the first and second biosensors of the invention is not particularly limited, either. Hereinafter, a preferred embodiment of a method to produce the second biosensor of the invention will be described. The invention is not limited to the method described below. The production of the first biosensor of the invention is not particularly limited, either. For example, the production can be carried out in the same way except that the third reaction layer is not formed in the following description.

The first and third reaction layers 8 and 10 may be formed by any method, and the second reaction layer 9 is formed on the first reaction layer 8 by applying a solution containing lipid decomposing enzyme thereonto. The method for the application is not particularly limited, and may be a method of applying a lipid-decomposing-enzyme-containing solution by dropping the solution, or by use of a spray device, bar coater, die coater, reverse coater, comma coater, gravure coater, spray coater or doctor knife, or some other applying tool.

The method for forming the first and third reaction layers 8 and 10 is not particularly limited, and may be the same method as used to form the second reaction layer. The method for forming the second reaction layer 9 may be identical with or different from the method for forming the first and third reaction layers 8 and 10. Taking account of easiness of forming, production costs, and others, it is preferred to use the same method, in particular, a method of dropping each solution containing predetermined components to apply, and then drying the applied film. Such a method can produce a biosensor easily, and decrease production costs when biosensors can be mass-produced, then, it is preferable.

The first reaction layer is first formed as follows: a redox enzyme (for example, PQQ-dependent glycerol dehydrogenase) is mixed with desired components, such as a surfactant (for example, Emalgen) if necessary, and a glycylglycine buffer solution, to prepare a redox enzyme solution. A predetermined quantity of this redox enzyme solution is dropped onto electrodes (working regions). After the dropping of the prepared redox enzyme solution, the solution is dried inside a thermostat having a temperature kept at a predetermined value or on a hot plate, to form the first reaction layer on the electrodes (working regions). The surfactant may be included merely in the first reaction layer, or a layer containing the surfactant may be formed to cover the first reaction layer. Alternatively, a surfactant layer is formed on the electrodes, and then the first reaction layer 8 may be formed thereon. If necessary, the above-mentioned other components (for example, the hydrophilic polymer) may be added thereto. A volatile organic solvent such as ethanol may also be added thereto if necessary. The addition of volatile organic solvent makes the drying speedy, and restrains crystallizing over a small level. An adhesive may be beforehand applied onto the base plate 1.

When the surfactant layer is formed, a surfactant (for example, Emalgen PP-290 (manufactured by Kao Corp.) is mixed with desired components such as glycylglycine buffer solution, and a volatile organic solvent to prepare a surfactant solution. A predetermined quantity of this surfactant solution is dropped onto the electrodes or the first reaction layer. Alternatively, as will be described below, the quantity is to be dropped onto the second reaction layer, the third reaction layer or the cover 7. After dropping of the surfactant solution, the solution is dried inside a thermostat having a temperature kept at a predetermined value, or on a hot plate to form the surfactant layer.

The second reaction layer is next formed as follows: A lipid decomposing enzyme (for example, lipoprotein lipase (LPL)) is mixed with desired components, such as glycylglycine buffer solution, to prepare a lipid decomposing enzyme solution. A predetermined quantity of this lipid decomposing enzyme solution is dropped onto the redox enzyme layer formed as described above. After dropping of the prepared lipid decomposing enzyme solution, the solution is dried inside a thermostat having a temperature kept at a predetermined value, or on a hot plate to form the second reaction layer on the first reaction layer. A surfactant may be further added to the second reaction layer. The surfactant may be included merely in the second reaction layer, or a layer containing the surfactant may be formed to cover the second reaction layer, as described above. If necessary, the above-mentioned other components (for example, the hydrophilic polymer) may be added thereto. If necessary, a volatile organic solvent such as ethanol may also be added thereto. The addition of volatile organic solvent makes the drying speedy, and restrains crystallizing over a small level.

The third reaction layer is formed as follows: An electron carrier (for example, hexaammineruthenium (III) chloride) is mixed with desired components, such as a surfactant (for example, Emalgen) if necessary, and a glycylglycine buffer solution, to prepare an electron carrier solution. A predetermined quantity of this electron carrier solution is dropped onto the cover 7. After dropping of the prepared electron carrier solution, the solution is dried inside a thermostat having a temperature kept at a predetermined value or on a hot plate, to form the third reaction layer on the cover. The surfactant may be included merely in the reaction layer, or a layer containing the surfactant may be formed to cover the reaction layer, as described above. Alternatively, it is allowable to form the surfactant layer onto the cover, and then form the third reaction layer 10 thereon. An adhesive may be beforehand applied onto the cover 7.

Finally, the base plate 1 on which the first and second reaction layer 8 and 9 are formed is bonded through adhesives 6a and 6b onto the cover 7 on which the third reaction layer 10 is formed. In this way, a second biosensor can be produced.

<Use of Biosensor>

A sample used in the invention is preferably in a solution form. The solvent in the solution form is not particularly limited, and may be a solvent selected with appropriate reference to conventionally known solvents, or obtained by combining two or more thereof.

The sample is not particularly limited, and is, for example, a living body sample such as whole blood, blood plasma, blood serum, saliva, urine or bone marrow; a drink such as juice, or a food product such as soy sauce or sauce; or drainage, rainy water, or pool water. The sample is preferably whole blood, blood plasma, blood serum, saliva, or bone marrow, and is more preferably whole blood.

About the sample, it is allowable to use an original liquid as it is, or a solution obtained by diluting an original liquid with an appropriate solvent to adjust the viscosity or some other properties thereof. The substrate contained in the sample is not particularly limited, and may be any substance as far as the substance is reactive with the respective enzymes contained in the first and second reaction layers of the invention to generate a measurable current which will also be described later.

Examples of the desired component (substrate) in the sample include saccharides such as glucose, polyhydric alcohols such as glycerol, sorbitol, and arabitol, lipids such as neutral fat and cholesterol, organic acids such as glutamic acid and lactic acid, creatine, and creatinine. For the same reason as described above, it is preferred to select a lipid such as neutral fat or cholesterol, as the substrate.

The manner to supply the sample into the sample-supplying section is not particularly limited. For example, the sample may be supplied to the reaction layers (the first, second and third reaction layers 8, 9 and 10) from a horizontal side thereof by capillary phenomenon.

When the sample is supplied to the reaction layers (the first, second and third reaction layers 8, 9 and 10), the desired component (substrate) in the sample is oxidized by the effect of lipid decomposing enzyme contained in the second reaction layer 9 and redox enzyme contained in the first reaction layer 8. At the same time when the substrate itself is oxidized, electrons are emitted therefrom. The electrons emitted from the substrate are captured by the electron carrier dissolved out from the third reaction layer 10. Following this, the electron carrier changes from oxidized form to reduced form. After addition of the sample, by leaving the biosensor over a predetermined period, the substrate is completely oxidized by the lipid decomposing enzyme and the redox enzyme. Thus, a certain quantity of the electron carrier is converted from an oxidized form to a reduced form.

The biosensor of the invention can significantly shorten the reaction time (that is, the measuring time), in which the reaction between the substrate and the enzyme is completed. The reaction time (that is, the measuring time), in when the reaction between the substrate and the enzyme is completed, is not particularly limited. After the addition of the sample, the reaction time is usually from 1 to 120 seconds, preferably from 1 to 90 seconds, more preferably from 1 to 60 seconds, in particular preferably from 1 to 45 seconds.

Thereafter, in order to oxidize the electron carrier in a reduced-form, a predetermined potential is applied to the working electrode 2 and the counter electrode 4 through the electrodes. Thereby, the reduced-form electron carrier is electrochemically oxidized to be converted into an oxidized-form. By the value of a current measured at this time (the current may be referred to as the "oxidation current" hereinafter), the quantity of the reduced-form electron carrier before the potential is applied is calculated out. Furthermore, the quantity of the substrate that has reacted with the enzymes can be quantitatively determined. The value of the potential applied when the oxidation current flows is not particularly limited, and may be appropriately adjusted with reference to conventionally known findings. For example, it is advisable to apply a potential of about −200 to +700 mV, preferably 0 to +500 mV between the counter electrode 4 and the working electrode 2. The potential-applying means to apply the potential is not particularly limited, and may be a conventionally known appropriate potential-applying means.

The manner to measure the oxidation current value and the manner to convert the current value to the substrate concentration may be chronoamperometry, in which the current value is measured after a certain period from applying a predetermined potential, or chronocoulometry, in which a measurement is made about the quantity of charges that is obtained by integrating the current response by chronoamperometry with respect to time. Chronoamperometry is preferably used because the measurement can be attained with a simple device system.

An example, in which the concentration of substrate is calculated out by measuring a current by oxidization of reduced-form electron carrier (oxidation current), has described as above. As the case may be, it is allowable to adopt an embodiment that the concentration of substrate is calculated out by measuring a current by reduction of oxidized-form electron carrier remaining unreduced (reduction current).

The biosensor of the invention may be used in any form without any special limitation. The biosensor may be used for various applications, such as a disposable-type biosensor, which is a disposable article, and a biosensor to measure a predetermined value continuously by embedding at least electrodes in a human body.

The biosensor of the invention may be applied to a conventionally known sensor, such as a neutral fat sensor or a cholesterol sensor.

The advantageous effects of the invention are summarized as follows.

By the biosensor of the invention, redox enzyme and lipid decomposing enzyme are contained separately in different reaction layers each other; thus, as well as decomposition of neutral fat to glycerol by the lipid decomposing enzyme, oxidation reaction by the redox enzyme advances rapidly. For this reason, the concentration of glucose or neutral fat in sample can be measured in a short time. Measured values are hardly varied, thus, the biosensor is further improved in measurement precision.

EXAMPLE

The advantageous effects of the invention will be described by way of the following Examples and Comparative Example. However, the technical scope of the invention is not limited to only the following Examples. The symbol "%" denotes "% by mass" unless otherwise specified.

Measurement of Neutral Fat Concentration in Whole Blood

Example 1

For electrodes, use was made of a chip, DEP Chip EP-N (manufactured by Bio Device Technology Co., Ltd.) was used. In DEP Chip EP-N, working electrode 2, reference electrode 3 and counter electrode 4 each made of carbon were formed on insulating base plate 1, and, via insulating layer 5, the followings were formed: working region of working electrode 2-1 made of carbon, working region of reference electrode 3-1 made of silver/silver chloride, and working region of counter electrode 4-1 made of carbon.

A first reaction layer (GLDH layer) was formed through the following steps.

PQQ-dependent glycerol dehydrogenase, glycylglycine (manufactured by Wako Pure Chemical Industries, Ltd.), and Emalgen PP-290 (manufactured by Kao Corp.) were mixed to give final concentrations of 1.5 U, 5 mM (0.65 μg) and 0.025% (0.5 μg), respectively, per sensor (volume of "whole blood" sample to be supplied: 2 μl), and to yield a solution (GLDH solution). The resultant GLDH solution was dropped onto EP-N to cover the working region of working electrode, the working region of reference electrode, and the working region counter electrode. The solution was dried at 30° C. for 5 minutes to yield the first reaction layer (GLDH layer).

A second reaction layer (LPL layer) was formed through the following steps.

lipoprotein lipase (LPL) (manufactured by Asahi Kasei Corp.), and glycylglycine (manufactured by Wako Pure Chemical Industries, Ltd.) were mixed so as to have concentrations of 75 U and 5 mM (0.65 μg), respectively, per sensor (sample liquid volume: 2 μl), and to yield a solution (LPL solution). The resultant LPL solution was dropped onto the formed GLDH layer to be superposed on the layer (for covering). The solution was dried at 30° C. for 5 minutes to yield the second reaction layer (LPL layer).

In this way, the LPL layer, which was the second layer, was formed (superposed) on the GLDH layer, which was the first layer.

A third reaction layer (electron carrier layer) was formed through the following steps.

Hexaammineruthenium (III) chloride (manufactured by Wako Pure Chemical Industries, Ltd.), glycylglycine (manufactured by Wako Pure Chemical Industries, Ltd.), and Emalgen PP-290 (manufactured by Kao Corp.) were mixed to give final concentrations of 100 mM (65 μg), 25 mM (3.25 μg) and 0.1% (2 μg), respectively, per sensor (volume of sample "whole blood" to be supplied: 2 μl), and to yield a mediator solution. The resultant mediator solution was dropped in a gap formed by affixing adhesives (double-sided tapes) onto a cover made of PET. The solution was then dried at 50° C. for 5 minutes to yield the third reaction layer (electron carrier layer).

The cover, on which the third reaction layer was formed, was bonded to the adhesives (double-sided tapes) stuck to the base plate, on which the first and second reaction layers were formed, to produce a neutral fat sensor. Properties thereof were evaluated. The thickness of each of the first, second and third reaction layers was 5 μm, and the separation distance between the second and third reaction layers was 0.15 mm.

Figure 5:
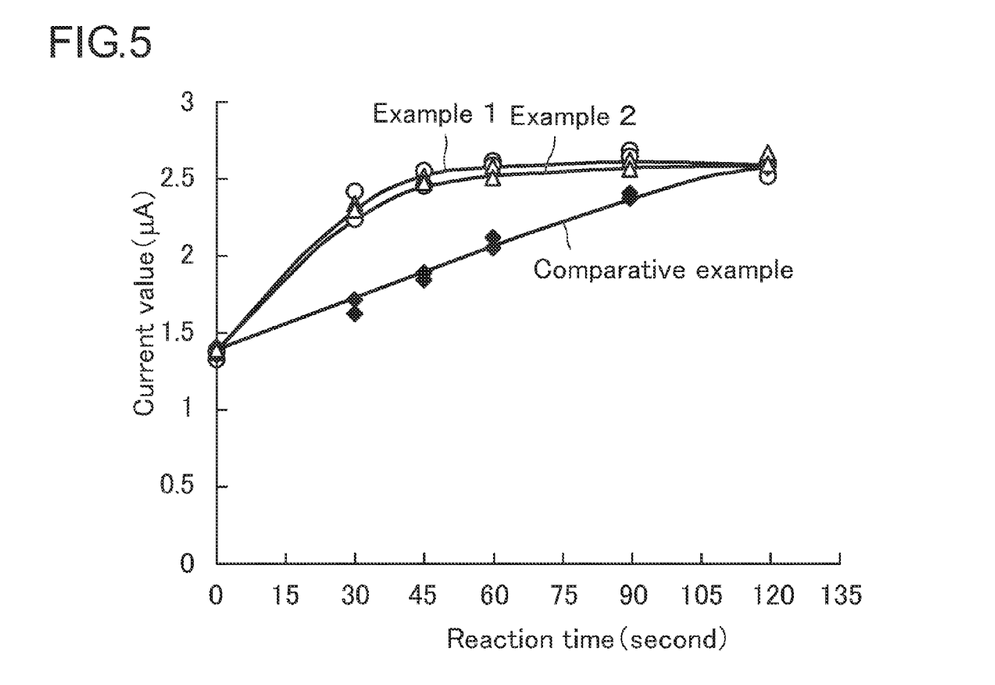

Two microliter of the sample liquid (whole blood; neutral fat value of 300 mg/dl) was absorbed thereto, and then allowed to be on standby over each seconds as reaction time. Thereafter, the reference electrode was used as a reference and a potential of +200 mV was applied between the working electrode and the counter electrode. After 5 seconds, the value of current flowing between the working electrode and the counter electrode was measured. This current value was in proportion to the concentration of the reduced electron carrier, that is, the concentration of decomposed neutral fat in the whole blood. From this current value, the neutral fat concentration in the whole blood can be determined. The results are shown in Table 1 and FIG. 5. In FIG. 5, the results of Example 1 are represented by white circle (○).

Example 2

A first reaction layer (GLDH layer) was formed in the same way as in Example 1.

A second reaction layer (electron carrier-containing LPL layer) was formed through the following steps.

Lipoprotein lipase (LPL, manufactured by Asahi Kasei Corp.), glycylglycine (manufactured by Wako Pure Chemical Industries, Ltd.), and hexaammineruthenium (III) chloride (manufactured by Wako Pure Chemical Industries, Ltd.) were mixed to give concentrations of 75 U, 5 mM (0.65 μg), and 100 mM (65 μg), respectively, per sensor (sample liquid volume: 2 μl) to yield a solution (electron carrier-containing LPL solution). The resultant electron carrier-containing LPL solution was dropped onto the formed GLDH layer to be superposed on the layer (for covering). The solution was dried at 30° C. for 5 minutes to yield the second reaction layer (electron carrier-containing LPL layer).

In this way, the electron carrier-containing LPL layer, which was the second layer, was formed (superposed) on the GLDH layer, which was the first reaction layer.

A surfactant layer was formed through the following steps.

Glycylglycine (manufactured by Wako Pure Chemical Industries, Ltd.) and Emalgen PP-290 (manufactured by Kao Corp.) were mixed to give final concentrations of 25 mM (3.25 μg) and 0.01 (2 μg), respectively, per sensor (volume of sample "whole blood" to be supplied: 2 μl), and to yield a surfactant solution. The resultant surfactant solution was dropped into a gap formed by affixing adhesives (double-sided tapes) onto a cover made of PET. The solution was then dried at 50° C. for 5 minutes to yield a surfactant layer.

The cover, on which the surfactant layer was formed, was bonded to the adhesives (double-sided tapes) stuck to the base plate, on which the first and second reaction layers were formed, to produce a neutral fat sensor. Properties thereof were evaluated. The thickness of each of the first and second reaction layers and the surfactant layer was 5 μm, and the separation distance between the second reaction layer and the surfactant layer was 0.15 mm.

About the neutral fat sensor produced as above, the current value thereof was measured in the same way as in Example 1. The results are shown in Table 1, and FIG. 5. In FIG. 5, the results of Example 2 are represented by white triangle (Δ).

Comparative Example

A GLDH solution and a LPL solution were prepared in the same way as in Example 1. Next, the GLDH solution and the LPL solution were mixed with each other to make the amount of each of the components per sensor (volume of "whole blood" sample to be supplied: 2 μl) equal to that in each of the Example. The mixed liquid was dropped onto EP-N chip to cover its working region of working electrode, working region of reference electrode, and working region of counter electrode. The solution was dried at 30° C. for 5 minutes to yield a mixed layer of GLDH layer and LPL layer. Except these steps, in the same way as in Example 1, a comparative neutral fat sensor was produced.

About the neutral fat sensor produced as above, the current value thereof was measured in the same way as in Example 1. The results are shown in Table 1, and FIG. 5. In FIG. 5, the results of Comparative Example 1 are represented by black square (♦).

Example 3

Electrodes used therein were three-electrode-system electrodes designed and produced by the inventors themselves. In the electrode system, working electrode 2, reference electrode 3 and counter electrode 4 each made of carbon were formed on insulating base plate 1, and via insulating layer 5, the following were formed: working region of working electrode 2-1 made of carbon, working region of reference electrode 3-1 made of silver/silver chloride, and working region of counter electrode 4-1 made of carbon.

A first reaction layer (GLDH layer) was formed through the following steps.

PQQ-dependent glycerol dehydrogenase, glycylglycine (manufactured by Wako Pure Chemical Industries, Ltd.), Emalgen PP-290 (manufactured by Kao Corp.), and polymer Polyethylene Glycol 6000 as a hydrophilic polymer were mixed to give final concentrations of 1.0 U, 10 mM (1.3 μg), 0.05% (0.5 μg), and 0.75% (7.5 μg), respectively, per sensor (volume of "whole blood" sample to be supplied: 1 μl) to yield a solution (GLDH solution). The resultant GLDH solution was dropped onto the electrodes to cover their working region of working electrode, working region of reference electrode, and working region of counter electrode. The solution was dried at 40° C. for 5 minutes to yield the first reaction layer (GLDH layer).

A second reaction layer (electron carrier-containing LPL layer) was formed through the following steps.

Lipoprotein lipase (LPL, manufactured by Asahi Kasei Corp.), glycylglycine (manufactured by Wako Pure Chemical Industries, Ltd.), and hexaammineruthenium (III) chloride (manufactured by Wako Pure Chemical Industries, Ltd.) were mixed to give final concentrations of 80 U, 5 mM (0.65 μg), and 200 mM (61.9 μg), respectively, per sensor (sample liquid volume: 1 μl) to yield a solution (electron carrier-containing LPL solution). The resultant electron carrier-containing LPL solution was dropped onto the formed GLDH layer to be superposed on the layer (for covering). The workpiece was dried at 40° C. for 5 minutes to yield the second reaction layer (electron carrier-containing LPL layer).

In this way, the electron carrier-containing LPL layer, which was the second layer, was formed (superposed) on the GLDH layer, which was the first reaction layer.

A surfactant layer was formed through the following steps.

The cover, on which the surfactant layer was formed, was bonded to the adhesives (double-sided tapes) stuck to the base plate, on which the first and second reaction layers were formed, to produce a neutral fat sensor. Properties thereof were evaluated. The thickness of each of the first and second and third reaction layers and the surfactant layer was 5 μm, and the separation distance between the second reaction layer and the surfactant layer was 0.1 mm.

Figure 6:
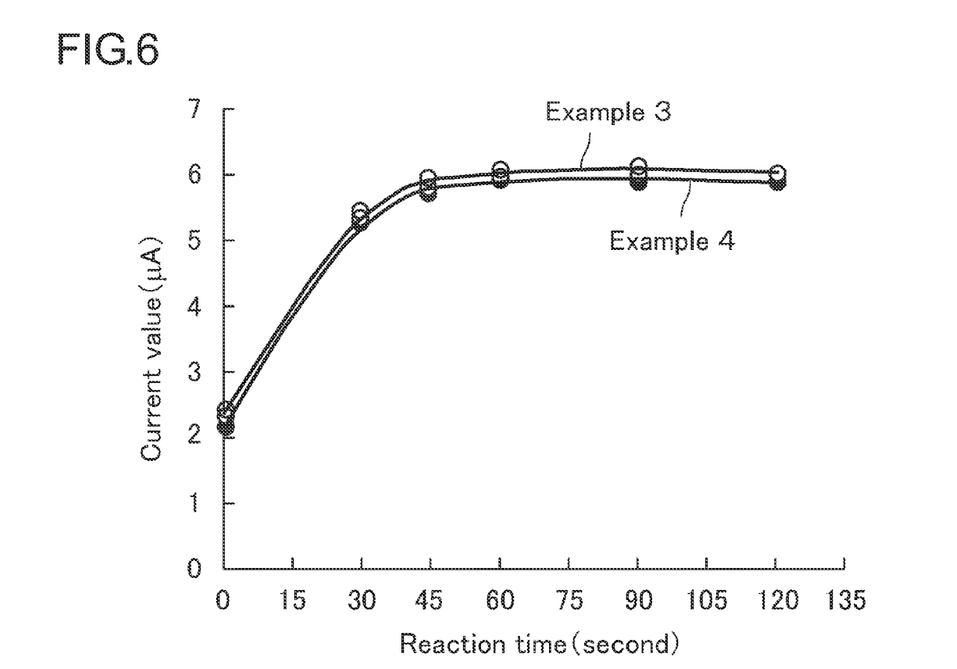

The neutral fat sensor produced as above was evaluated as follows: One microliter of the sample liquid (the whole blood; neutral fat value of 183 mg/dl) was absorbed thereto, and then allowed to be on standby over each seconds as a reaction time. Thereafter, the reference electrode was used as a reference and to apply a potential of +200 mV was applied between the working electrode and the counter electrode. After one second, the value of current flowing between the working electrode and the counter electrode was measured. This current value is in proportion to the concentration of the reduced electron carrier, that is, the concentration of decomposed neutral fat in the whole blood. From this current value, the neutral fat concentration in the whole blood can be determined. The results are shown in Table 1, and FIG. 6. In FIG. 6, the results of Example 3 are represented by white circle (◯).

Example 4

The value of current was measured in the same way as in Example 3 except that, instead of 0.75% (7.5 µg) of Polyethylene Glycol 6000 in Example 3, Polyvinyl Alcohol 500 (manufactured by Wako Pure Chemical Industries, Ltd.) of the same concentration was used. The results are shown in Table 1, and FIG. 6. In FIG. 6, the results of Example 4 are represented by black circle (●).

Example 5

Figure 7:
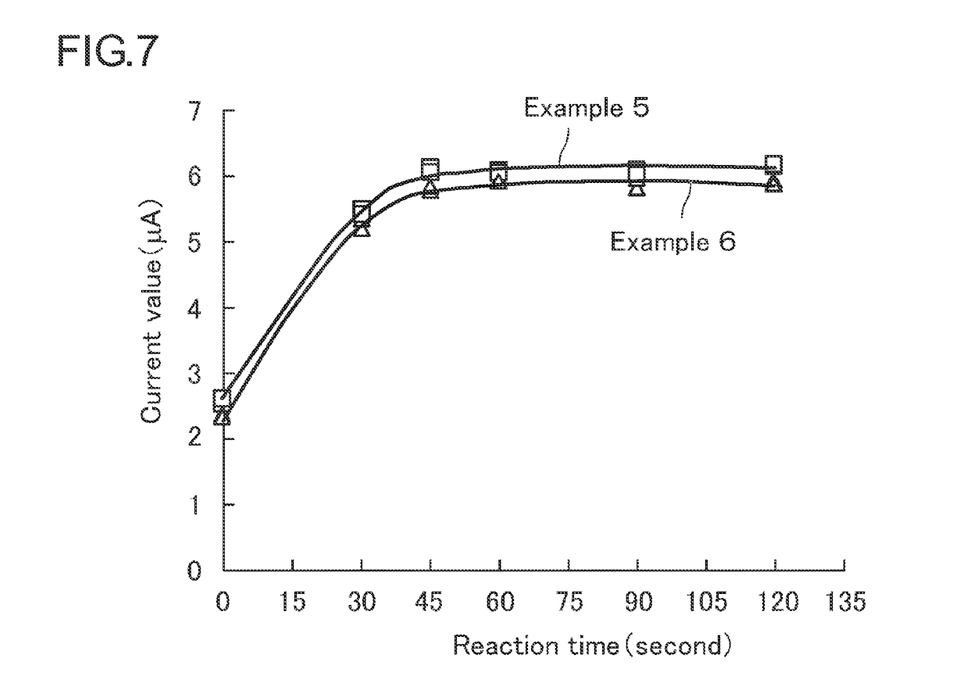

The value of a current was measured in the same way as in Example 3 except that, instead of 0.75% (7.5 µg) of Polyethylene Glycol 6000 in Example 3, 10% (100 µg) of trehalose (manufactured by Wako Pure Chemical Industries, Ltd.) was used. The results are shown in Table 1, and FIG. 7. In FIG. 7, the results of Example 5 are represented by white square (□).

Example 6

The value of current was measured in the same way as in Example 3 except that, instead of 0.75% (7.5 µg) of Polyethylene Glycol 6000 in Example 3, 1% (10 µg) of BSA (manufactured by Wako Pure Chemical Industries, Ltd.) was used. The results are shown in Table 1, and FIG. 7. In FIG. 7, the results of Example 6 are represented by white triangle (Δ).

would be based on the following: LPL, which is lipid decomposing enzyme, has higher solubility than GLDH, which is redox enzyme; thus, when GLDH and LPL are present in a mixed state in the same layer as in the comparative neutral fat sensor of Comparative Example, the low solubility of GLDH affects the solubility of LPL, thereby the total solubility falls. On the other hand, the neural fat sensor of the invention solves such a problem. As described in the Examples, by providing the two enzymes into different layers each other, LPL rapidly dissolves and starts reaction, and subsequently GLDH dissolves and starts reaction. It is assumed that, as a result, the separation of the two enzymes into different layers makes the total reactivity be enhanced, thereby the invention realizes the reduction in reaction time.

In Examples 3 to 6, the respective reaction times were 45 seconds, and these were as short as those in Examples 1 and 2. Accordingly, also in the case of including saccharide, protein or hydrophilic polymer in at least one of the first, second and third reaction layers, the excellent effect of shortening reaction time is obtained.

EXPLANATION OF REFERENCE SIGN

1 Insulating base plate
2 Working electrode
2-1 Working region of working electrode
3 Reference electrode
3-1 Working region of Reference electrode
4 Counter electrode
4-1 Working region of Counter electrode
5 Insulating layer
6 (6a and 6b) Adhesive
7 Cover
8 First reaction layer
9 Second reaction layer
10 Third reaction layer
S Space

The invention claimed is:

TABLE 1

| Reaction time (seconds) | Current value (µA) | | | | | | |
|---|---|---|---|---|---|---|---|
| | Example 1 | Example 2 | Comparative Example | Example 3 | Example 4 | Example 5 | Example 6 |
| 0 | 1.373 | 1.384 | 1.355 | 2.445 | 2.246 | 2.505 | 2.384 |
|  | 1.330 | 1.391 | 1.406 | 2.364 | 2.197 | 2.613 | 2.369 |
| 30 | 2.412 | 2.345 | 1.713 | 5.334 | 5.288 | 5.519 | 5.217 |
|  | 2.237 | 2.299 | 1.628 | 5.477 | 5.313 | 5.445 | 5.366 |
| 45 | 2.547 | 2.509 | 1.844 | 5.898 | 5.796 | 6.173 | 5.802 |
|  | 2.449 | 2.478 | 1.900 | 5.989 | 5.704 | 6.088 | 5.849 |
| 60 | 2.580 | 2.579 | 2.062 | 6.093 | 5.899 | 6.101 | 5.918 |
|  | 2.613 | 2.506 | 2.125 | 5.960 | 5.915 | 6.079 | 5.933 |
| 90 | 2.673 | 2.631 | 2.409 | 6.015 | 5.942 | 6.131 | 5.831 |
|  | 2.639 | 2.567 | 2.377 | 6.125 | 5.877 | 6.069 | 5.976 |
| 120 | 2.513 | 2.671 | 2.571 | 6.062 | 5.952 | 6.177 | 5.945 |
|  | 2.597 | 2.598 | 2.616 | 6.043 | 5.913 | 6.192 | 5.899 |

As is evident from Table 1, and FIGS. 5, 6 and 7, it is understood that the time until the current value measured in the comparative neutral fat sensor of Comparative Example reached an equilibrium state was about 120 seconds, while the time until the current value measured in the neutral fat sensor of each of Examples 1 to 6 reached an equilibrium state was about 45 seconds. These results evidently demonstrate that the use of the biosensor of the invention makes it possible to measure neutral fat in a shorter time than that of biosensors in the prior art. The results of the Comparative Example 1. A biosensor, comprising an insulating base plate, an electrode system containing at least a working electrode and a counter electrode and formed on the insulating base plate, and a sample-supplying section formed on the electrode system, wherein the sample-supplying section has a reaction layer comprising:

a first reaction layer formed on the electrode system and containing at least a redox enzyme into which pyrroloquinoline quinone (PQQ), flavin adenine dinucleotide (FAD), or flavin mononucleotide (FMN) is incorporated as a prosthetic group; and a second reaction layer formed by applying, onto the first reaction layer, a solution including a lipid decomposing enzyme.

2. The biosensor according to claim 1, wherein the sample-supplying section further comprises an electron carrier.

3. The biosensor according to claim 2, wherein the electron carrier is located in the second reaction layer, or a third reaction layer having the electron carrier is further provided in the sample-supplying section to be separated from the first and second reaction layers.

4. The biosensor according to claim 1, wherein the redox enzyme is polyol dehydrogenase into which pyrroloquinoline quinone (PQQ) is incorporated as the prosthetic group.

5. The biosensor according to claim 3, wherein the first, second, or third reaction layer further comprises a surfactant.

6. The biosensor according to claim 3, wherein the first, second, or third reaction layer further comprises a hydrophilic polymer.

7. The biosensor according to claim 3, wherein the first, second, or third reaction layer further comprises at least one of saccharide and protein.

8. The biosensor according to claim 2, wherein the redox enzyme is polyol dehydrogenase into which pyrroloquinoline quinone (PQQ) is incorporated as the prosthetic group.

9. The biosensor according to claim 3, wherein the redox enzyme is polyol dehydrogenase into which pyrroloquinoline quinone (PQQ) is incorporated as the prosthetic group.

10. The biosensor according to claim 4, wherein the first, second, or third reaction layer further comprises a surfactant.

11. The biosensor according to claim 8, wherein the first, second, or third reaction layer further comprises a surfactant.

12. The biosensor according to claim 9, wherein the first, second, or third reaction layer further comprises a surfactant.

13. The biosensor according to claim 4, wherein the first, second, or third reaction layer further comprises a hydrophilic polymer.

14. The biosensor according to claim 5, wherein the first, second, or third reaction layer further comprises a hydrophilic polymer.

15. The biosensor according to claim 8, wherein the first, second, or third reaction layer further comprises a hydrophilic polymer.

16. The biosensor according to claim 9, wherein the first, second, or third reaction layer further comprises a hydrophilic polymer.

17. The biosensor according to claim 10, wherein the first, second, or third reaction layer further comprises a hydrophilic polymer.

18. The biosensor according to claim 11, wherein the first, second, or third reaction layer further comprises a hydrophilic polymer.

19. The biosensor according to claim 12, wherein the first, second, or third reaction layer further comprises a hydrophilic polymer.

20. The biosensor according to claim 4, wherein the first, second, or third reaction layer further comprises at least one of saccharide and protein.

* * * * *